(12) United States Patent
Nicola et al.

(10) Patent No.: US 7,605,106 B2
(45) Date of Patent: Oct. 20, 2009

(54) TELOMERIZATION OF DIENES

(75) Inventors: Antonio Pietro Nicola, Calgary (CA); Andrzej Krzywicki, Calgary (CA)

(73) Assignee: Nova Chemicals (International) S.A. (CH)

( * ) Notice: Subject to any disclaimer, the term of this patent is extended or adjusted under 35 U.S.C. 154(b) by 570 days.

(21) Appl. No.: 11/274,217

(22) Filed: Nov. 15, 2005

(65) Prior Publication Data

US 2007/0112238 A1  May 17, 2007

(51) Int. Cl.
| | |
|---|---|
| B01J 31/00 | (2006.01) |
| B01J 23/56 | (2006.01) |
| B01J 23/44 | (2006.01) |
| B01J 23/00 | (2006.01) |
| B01J 23/02 | (2006.01) |

(52) U.S. Cl. .............. 502/172; 502/170; 502/173; 502/332; 502/333; 502/334; 502/339; 502/350

(58) Field of Classification Search ............ 502/170, 502/172, 173, 333, 334, 339
See application file for complete search history.

(56) References Cited

U.S. PATENT DOCUMENTS

| | | | | | |
|---|---|---|---|---|---|
| 2,760,912 | A | * | 8/1956 | Schwarzenbek ........... 208/138 |
| 2,818,393 | A | * | 12/1957 | LeFrancois et al. ......... 502/334 |
| 3,509,209 | A | * | 4/1970 | Fenton ....................... 562/522 |
| 3,758,551 | A | * | 9/1973 | Murib et al. ................ 560/208 |
| 3,900,386 | A | * | 8/1975 | Hayes ..................... 208/111.1 |
| 3,992,456 | A | * | 11/1976 | Atkins et al. ................ 568/898 |
| 4,093,559 | A | * | 6/1978 | Fernholz et al. ............ 502/170 |
| 4,417,079 | A | | 11/1983 | Yoshimura et al. .......... 568/903 |
| 5,030,792 | A | | 7/1991 | Slaugh ....................... 585/639 |
| 6,030,921 | A | * | 2/2000 | Ziemer ...................... 502/325 |
| 6,492,299 | B1 | * | 12/2002 | Couves et al. ............... 502/339 |
| 6,548,445 | B1 | * | 4/2003 | Buysch et al. ............... 502/230 |
| 7,030,286 | B2 | * | 4/2006 | Rottger et al. .............. 585/514 |

FOREIGN PATENT DOCUMENTS

| | | | |
|---|---|---|---|
| JP | 54-082392 | * | 6/1979 |
| WO | WO 92/10450 | | 6/1992 |

OTHER PUBLICATIONS

"Telomerization of butadiene with water catalyzed by heterogenous palladium catalysts," Byoung In Lee et al. Journal of Molecular Catalysis A: Chemical 156(2000), pp. 183-187.*

* cited by examiner

*Primary Examiner*—Patricia L Hailey
(74) *Attorney, Agent, or Firm*—Kenneth H. Johnson

(57) ABSTRACT

Alkadienes may be telomerized in the presence of a heterogeneous catalyst comprising an alumina or titania support which is modified with one or more ionic complexes of Pd or Pt and activated at a temperature from 450° C. to 850° C. for a time not less than two hours. The resulting telomere may be useful in a number of applications.

7 Claims, No Drawings

TELOMERIZATION OF DIENES

FIELD OF THE INVENTION

The present invention relates to a process for the telomerization (dimerization) of alkadienes (e.g. butadiene or isoprene) to precursors of 1-substituted octanes such as a 2,7-octadiene 1-functional molecule. The functionality may be alcohol, ether or ester. More particularly the present invention relates to the use of a heterogeneous catalyst (i.e. supported) for such telomerization.

BACKGROUND OF THE INVENTION

There are a number of routes to produce higher linear alpha olefins. Traditionally lower olefins such as ethylene have been oligomerized in the presence of aluminum alkyl catalysts to yield a mixture of higher alpha olefins. The mixture must then be separated to yield different higher linear alpha olefins (LAO's). The process is not particularly selective and one can't use it to make on demand higher linear alpha olefins. Unfortunately the demand for various higher linear alpha olefins changes with time and it is difficult to shift the equilibrium to selectively produce a particular alpha olefin in a high yield.

Phillips developed a catalyst/process to selectively convert ethylene to 1-hexene. This meets a need for 1-hexene such as in the gas phase or slurry phase polymerization of ethylene hexene copolymers. However, for solution phase polymerization a significant copolymer tends to be 1-octene rather than 1-hexene.

Kuraray, Dow, Shell and Oxeno have over the last thirty years developed various homogeneous (i.e. non-supported catalyst) processes to telomerize/dimerize butadiene in the presence of a polar compound such as water, an alcohol or an acid, a stabilizing ligand and a group 9 or 10, preferably 10, metal, most preferably Pd and Pt to produce octadiene with a terminal functional group such as an alcohol, ether or ester (telomere). After the hydrogenation of the double bonds the functional group may be removed from the telomere typically in the presence of an acid catalyst (e.g. alumina) resulting in the formation of 1-octene. Representative of these types of processes are U.S. Pat. No. 4,417,079 issued Nov. 22, 1983 to Yoshimura et al., assigned to Kuraray Company Limited; U.S. Pat. No. 5,030,792 issued Jul. 9, 1991 to Slaugh, assigned to Shell Oil Company; and WO 92/10450 published Jun. 25, 1992 in the name of Bohley et al., assigned to Dow Benelux N. V. This art uses an unsupported catalyst which is soluble in the reaction medium (homogeneous catalyst). Metals such as Rh, Pd, and Pt are extremely expensive and any loss of the catalyst has a strong negative impact on the economics of the process.

The present invention seeks to provide a process for the telomerization of alkadienes to octadiene substituted in position 1 with a functional group containing an oxygen atom (typically an alcohol or ether) in the presence of a stable heterogeneous (i.e. supported) catalyst from which there is only a very low loss of metal.

SUMMARY OF THE INVENTION

The present invention provides a method for preparing a heterogeneous catalyst precursor suitable for the telomerization of $C_{4-8}$ hydrocarbyl dienes with an oxygenated compound containing active hydrogen atoms compounds, such as alcohols, esters or organic acids, comprising impregnating a solid alumina or titanium oxide support with one or more ionic complex of a metal selected from the group consisting of Pd and Pt from a medium selected from the group consisting of water, $C_{1-4}$ alcohols, $C_{1-4}$ ketones, $C_{1-4}$ carboxylic acids (acetic acid), and $C_{6-10}$ aromatic hydrocarbyl compounds which are unsubstituted or substituted by one or more $C_{1-4}$ alkyl radicals, to provide from 0.05 to 5 weight % of said metal based on the total weight of the oxide support used, drying the impregnated supported catalyst at a temperature from 20° C. to 100° C. and a pressure of less than or equal to 101 kPa for a minimum of 2 hours, and heating the resulting impregnated support in an oxidizing atmosphere (e.g. air) at a temperature from 450° C. to 850° C. for a time not less than two hours.

The present invention further provides a process for the telomerization of one or more $C_{4-8}$ hydrocarbyl diene in a stream comprising not less than 5 weight % of said diene, optionally a solvent, from 0.0005 to 0.01 equivalents per mole of diene in the feedstock of one or more electron donors, from 0.05 to 0.5 weight % of an activator, and not less than 15 weight % based on the weight of said diene of one or more oxygenated compounds containing active hydrogen atoms comprising contacting said stream with a bed of catalyst comprising oxides of one or more metals selected from the group consisting of Pd and Pt deposited on a solid support to provide from 0.1 to 5 weight % of said metal based on the weight of the support, at a temperature from 20° C. to 150° C. and a pressure from 34.45 kPa to 3,445 kPa with a residence time between 10 minutes and 10 hours and separating the resulting telomere from said stream.

DETAILED DESCRIPTION

The catalysts of the present invention are prepared by the impregnation or incipient wetness impregnation of a support, typically an oxide support. The support may be alumina ($Al_2O_3$) or titania (titanium dioxide). Typically, the support is in the form of particles having an average particle size from 5 to 25 mesh or spheres between 2 to 10 mm diameter, or extrudates from 1/16" to 1/4". The support will have a surface area greater than 20 $m^2/g$, preferably greater than 50 $m^2/g$, most preferably greater than 100 $m^2/g$, and a pore volume from about 0.1 to 1.3, preferably from 0.2 to 1.2, most preferably from 0.3 to 1.1 ml/g.

The starting palladium (Pd) and platinum (Pt) compounds need to be ionic complexes or salts soluble or dispersible in the medium and which on heating become activated. As examples of platinum compounds, there may be mentioned platinum $C_{1-6}$ carboxylates, preferably $C_{1-4}$ carboxylates and particularly, platinum acetate, platinum (II) halides and in particular platinum (II) chloride, platinum (IV) halides and in particular platinum (IV) chloride, platinum (II) alkali halides such as platinum (II) potassium chloride, platinum (IV) alkali halides such as platinum (IV) potassium chloride, platinum acetylacetonate. Palladium compounds include, for example palladium $C_{1-6}$ carboxylates such as palladium citrate, preferably $C_{1-4}$ carboxylates such as palladium acetate, palladium carbonate, palladium halides such as palladium chloride, palladium nitrate, palladium sulfate, palladium acetylacetonate, alkali tetrahalogen palladium compounds such as sodium tetrachloropalladium, etc. One useful complex is palladium acetate.

The ionic complex is dissolved or dispersed in a medium selected from the group consisting of water, alcohols, preferably $C_{1-4}$ alcohols, ketones, preferably $C_{1-4}$ ketones, carboxylic acids, preferably $C_{1-6}$, most preferably $C_{1-4}$ carboxylic acids (acetic acid and citric acid), and aromatic hydrocarbyl compounds preferably aromatic $C_{6-10}$ hydrocarbyl compounds which are unsubstituted or substituted by one or more $C_{1-4}$ alkyl radicals. Preferably the medium is selected from the group consisting of benzene, toluene, methanol, ethanol, propanol, butanol, water and mixtures thereof.

The ionic complex is dissolved/dispersed in the medium in an amount to provide from 0.05 to 5 preferably from 0.1 to 1.5 weight % of the metal (e.g. Pd or Pt) based on the weight of the support. T he ionic complex is deposited on a catalyst support by impregnation although other suitable procedures such as spray drying could be used. Typically the support is immersed in the medium for a short period of time, typically less than 5 hours, preferably less than 1 hour most preferably less than half an hour. It is desirable that the support becomes fully impregnated with the solution/dispersion of the ionic complex.

The impregnated support is then dried generally at temperatures from 20° C. to 100° C., typically from 50° C. to 100° C., preferably from 75° C. to 100° C. and a pressure of less than or equal to 101 kPa, preferably less than 50 KPa, for a minimum of 2 hours. Depending on the temperature and pressure drying times from 2 to 30 hours may be used.

The dried impregnated support is then activated in an oxidizing atmosphere such as air at a temperature from 450° C. to 850° C. for a time not less than two hours. Generally, the catalyst may be activated at a temperature from 500° C. to 850° C. for a time from 2 to 72 hours. The complex decomposes at these temperatures and forms ionic complexes of Pd or Pt on support (alumina or titania). The catalyst may be regenerated by re-activation in an oxidizing atmosphere. Generally, the complex on the support is activated (calcined) at temperatures above 400° C., preferably between 450 and 850° C.

The catalyst precursor generated above is used in the telomerization process in combination with an activator. The activator may present in an amount from 0.01 to 5, preferably 0.01 to 0.5, most preferably 0.05 to 0.5 weight % based on the weight of the feed stream. Activators include alkali and alkaline earth $C_{1-6}$, preferably $C_{1-4}$ alkoxylates and mixtures thereof. One activator is sodium methoxylate.

The telomerization reaction may be carried out directly in a diene-telomere mixture. Butadiene, isoprene or butadiene rich $C_4$ fraction (typical product from steam cracking operations) are the preferred dienes. The dienes or fractions containing corresponding dienes should be free of acetylenic compounds. The acetylenics compounds cause rapid deactivation of catalyst during telomerization. The reacting mixture may optionally contain a low boiling solvent such as a $C_{1-8}$ ketone. One readily commercially available ketone is acetone. The oxygenated compounds containing active hydrogen atoms (telomers) are added to the reaction mixture in amounts not less than 15 weight %, typically from 20 to 90 weight %, preferably from 20 to 80 weight %, preferably from 30 to 75 weight % based on the weight of the feed stream. Preferred telomers include $C_{1-4}$ alcohols such as methanol, ethanol, propanol and butanol, $C_{1-8}$, preferably $C_{1-4}$ carboxylic acids and mixtures thereof. Most preferably the telomere is selected from the group consisting of methanol, ethanol, propanol, butanol and mixtures thereof. One advantage of the present invention is that the solvent, feed and product may be readily separated by a fairly simple distillation.

The reaction mixture also contains an electron donor. The electron donor may be a $C_{1-6}$, preferably $C_{1-4}$ alkyl tertiary amine such as trimethyl amine or triethyl amine. The electron donor may be tertiary phosphine. The substituents on the phosphorus may be a $C_{3-6}$ alkyl radical or a $C_{6-10}$ aromatic radical. Some useful phosphines include triphenyl phosphine and tri t-butyl phosphine. The electron donor may be a mixture of the foregoing amines and phosphines. The selection of electron donor affects selectivity and productivity of the reaction. Triphenyl phosphine used with Pd catalyst gives higher selectivity and higher productivity but lower activity on regeneration of the catalyst. Triethyl amine gives a lower selectivity and a lower productivity but better activity on regeneration. The electron donor may be used in amounts from 0.0005 to 0.01 preferably from 0.001 to 0.008 equivalents (molar equivalents) per mole of alkadiene in the feedstock (e.g. butadiene).

Generally the reaction is carried out in liquid phase under pressure. The pressure may range from about 5 psi (34.45 kPa) to 500 psi (3,445 kPa), typically from about 50 psi (344.5 kPa) to 500 psi, preferably from 100 psi (68.94 kPa) to 300 psi (2,067 kPa). The reaction may be conducted at temperatures from room temperature up to the boiling temperature of the reacting mixture. Typical temperatures may range from 20° C. to 150° C., typically from 20° C. to 120° C. preferably from about 60° C. to about 100° C. The contact time may be selected to give the required conversion. The time may be from about 10 minutes to 10 hours, generally less than 5 hours, typically from about 20 minutes to about 2 hours. The process may be batch or may be continuous. Continuous operations are preferred.

The feed stream should be a hydrocarbyl stream containing not less than 5 weight %, typically, 15 weight %, preferably greater than 20 weight %, most preferably more than 30 weight % of one or more alkadienes. The other hydrocarbyl components in the feed stream should be inert or have a low reactivity with the catalyst system (e.g. catalyst precursor and the activator). The resulting product will be an octadiene 1-substituted derivative. Typically the product of telomerization has a very high amount 2,7-octadiene-1-substituted derivative. The solvent (if present) and alkadiene feedstock can be easily separated by distillation to separate the octadiene-1-substituted product. The functional group can be removed together with hydrogenation of one of the double bonds to yield 1-octene.

The present invention will now be illustrated by the following non-limiting examples.

Two commercial catalyst samples comprising 1% palladium on a support were purchased. The catalysts were sold for purposes other than telomerization of diene streams.

Several catalysts were prepared in accordance with the present invention. The starting palladium compound was palladium acetate. The support was commercially purchased alumina (two different sources) or titania ($TiO_2$) in one case. The palladium loading was either 1.0% or 0.1 weight % based on the weight of the support. The solvent/diluent was toluene. The impregnated support was recovered from the solvent/diluent by filtering or decanting and dried at a temperature from 20 to 100° C. at a pressure from 1 to 15 psia, for a time from 2 to 24 hours. The resulting precursor was then activated in air at the temperature specified in the table below for from 2 to 24 hours.

The telomerization reaction was conducted using a plug flow, fixed bed reactor. The feed stream comprised butadiene minimum 5 weight % based on the total feed. The reactions were conducted in the presence of an electron donor, either tertiary ethyl amine (TEA) or triphenyl phosphine (TPP). The reaction pressures was in the range of from 1,350 to 2,000 kPa The results of the various runs are shown in Table 1 below. In Table 1 in the column Activation or Regeneration Temperature, and an a after a trial indicates activation temperature and an r indicates a reactivation temperature. For the commercial samples there is no activation temperature nor were the samples regenerated.

TABLE 1

| Run Number 1 | Catalyst 2 | Activation or Regeneration Temperature (° C.) 3 | Reaction Temperature (° C.) 4 | Catalyst Time on Stream (hrs) 5 | BD Conv. (%) 6 | Selectivity to 1- and 3-Methoxy-Octadienes (%) 7 | Selectivity to 1-methoxy-octediene-2,7 (%) 8 |
|---|---|---|---|---|---|---|---|
| 1 | Commercial A | | 85 | 1 | 15.6 | 68.4 | 99.3 |
| 2 | | | | 2 | 23.6 | 70.4 | 99.3 |
| 3 | | | | 4 | 17.4 | 64 | 99.2 |
| 4 | | | 75 | 3 | 3.4 | 8.4 | 100 |
| 5 | | | 85 | 3 | 23.6 | 67.7 | 99.3 |
| 6 | | | 95 | 3 | 9.8 | 40.1 | 99.2 |
| 7 | Commercial B | | 85 | 1 | 59.1 | 69.1 | 94 |
| 8 | | | | 2 | 52.5 | 69.9 | 94.7 |
| 9 | | | | 4 | 35.6 | 67.7 | 96.7 |
| 10 | | | | 6 | 18.5 | 62.3 | 98 |
| 11 | | | | 9 | 11.5 | 49.5 | 98.5 |
| 12 | 1% Pd/$Al_2O_3$ "S" | 500 | 85 | 1 | 58.6 | 69.8 | 93.8 |
| 13 | | | | 2 | 45.4 | 67.6 | 93.9 |
| 14 | | | | 4 | 29.6 | 66.3 | 94.8 |
| 15 | 1% Pd/$Al_2O_3$ "F" | 500 | 85 | 1 | 43.8 | 64.2 | 94.2 |
| 16 | | | | 2 | 53.5 | 60.4 | 94.5 |
| 17 | | | | 4 | 36.5 | 53.5 | 95.4 |
| 18 | | | | 6 | 28 | 49.5 | 96.4 |
| 19 | | | | 9 | 27.9 | 46.5 | 97.2 |
| 20 | | 500 | 65 | 4 | 83.1 | 69.3 | 96.5 |
| 21 | | | 75 | 4 | 76.9 | 64.4 | 95.5 |
| 22 | | | 85 | 4 | 63.2 | 64.9 | 94.5 |
| 23 | | 500a | 85 | 1 | 40 | 67.6 | 94.6 |
| 24 | | 500r1 | 85 | 1 | 54.1 | 67.3 | 94.4 |
| 25 | | 500r1 | 85 | 5 | 65.9 | 62.7 | 95.4 |
| 26 | | 500r2 | 85 | 1 | 61.4 | 68 | 95 |
| 27 | | 500r2 | 85 | 5 | 73.4 | 65 | 95.9 |
| 28 | | 700a | 85 | 1 | 56.7 | 67.7 | 93.8 |
| 29 | | 500r1 | 85 | 1 | 52.9 | 68.2 | 94.8 |
| 30 | | 500r2 | 85 | 1 | 53.6 | 68.2 | 96 |
| 31 | | 850a | 85 | 1 | 40 | 63.4 | 94.4 |
| 32 | | 500r1 | 85 | 1 | 30.7 | 64.2 | 95.8 |
| 33 | | 500r2 | 85 | 1 | 33.7 | 64 | 97.6 |
| 34 | 1% Pd on $TiO_2$ | 500 | 85 | 5 | 67.6 | 65.7 | 95.7 |
| 35 | 50 g cat. | 500r1 | 85 | 5 | 59 | 62.4 | 96.3 |
| 36 | | 500r2 | 85 | 5 | 48.2 | 60.2 | 96.9 |
| 37 | 100 g cat. | 500 | 85 | 1 | 51.3 | 66.8 | 93.9 |
| 38 | | | 85 | 3 | 84.3 | 65.1 | 94.7 |
| 39 | | | 85 | 5 | 83.7 | 64.3 | 95.2 |
| 40 | Control | 5 ppm Pd | 85 | | 14 | 31.3 | 95.5 |

Pressure - 2 MPa
Residence time of reacting mixture - 1 hour
Inert gas - nitrogen
S, F - indicate different commercial alumina samples
Control - homogeneous, liquid phase reaction with 5 ppm Pd. Activator and electron donor at the same amounts as for heterogeneous reaction.

The results in Table 1 show the examples of the present invention. All experiments except for comparative example 40, were performed in liquid phase, in the presence of solid catalysts in a continuous flow reactor system. After a catalyst was loaded in to the reactor, the system was purged for several hours with nitrogen at reaction temperature.

Runs 1-11

These examples show that two selected commercial catalysts containing 1% of palladium in a reduced form are active in the telomerization of butadiene with methanol. It has to be noted that with the increasing catalyst time on stream (Table 1, Column 5) butadiene conversion and overall selectivity to methoxy-octadienes decreased. However, the selectivity to 1-methoxy-octadiene-2,7 was improving, especially in the case of commercial catalyst "B".

Runs 4-6 show the impact of reaction temperature on butadiene conversion. Based on these results a reaction temperature of 85° C. was selected for comparative study of all catalysts apart from runs 20-22.

Runs 12-19

Two different commercial gamma-alumina supports were used to make catalysts according to the present invention containing 1% palladium on alumina. From this study is visible that the alumina "F" was a better support that was loosing activity (measured by butadiene conversion) slower than catalyst made on the base of alumina "S".

In both cases the selectivity of 1-methoxy-octadiene-2,7 was improving with catalyst time on stream.

Runs 20-22

These examples show that reaction temperature is an important factor. At lower temperature (65° C.) the highest butadiene conversion was achieved, although selectivity to methoxy-octadienes was comparable with other catalysts.

Runs 23-32

These runs show that regenerated catalysts treated in air at elevated temperatures maintain their activity during extended period of time. In some cases regenerated catalysts (runs 24-27) demonstrated higher activity in butadiene conversion than fresh activated catalyst (runs 15-18).

Runs 23, 28 and 31

Show initial catalyst activation should take place in an oxidative environment at elevated temperatures between 450 and 750° C. Activation at higher temperatures decrease catalyst activity which is not restored after regeneration at 500° C.

Runs 34-39

These results show that titania could be successfully used as catalyst support, although catalyst regeneration cycle do not recover initial catalyst activity.

The reaction is sensitive to the amount of catalyst used which indicates that by the removal of mass transfer limitations the butadiene conversion could be further improved.

Run 40

This control run was conducted to compare homogeneous butadiene telomerization with heterogeneous reactions under the same reaction conditions and the same residence time of 1 hour. It is clearly visible that butadiene conversion, and reaction selectivity towards methoxy-octadienes was significantly lower in the case of homogeneous reaction.

What is claimed is:

1. A method for preparing a heterogeneous catalyst precursor suitable for the telomerization of $C_{4-8}$ hydrocarbyl dienes with an oxygenated compound containing active hydrogen atom compounds consisting essentially of impregnating a solid alumina or titanium oxide support with a $C_{1-4}$ carboxylate, halide or acetylacetonate of a metal selected from the group consisting of Pd and Pt from a medium selected from the group consisting of water, $C_{1-4}$ alcohols, $C_{1-4}$ ketones, $C_{1-4}$ carboxylic acids, and $C_{6-10}$ aromatic hydrocarbyl compounds which are unsubstituted or substituted by one or more $C_{1-4}$ alkyl radicals, to provide from 0.05 to 5 weight % of said metal based on the total weight of oxide support used, drying the impregnated catalyst at a temperature from 20° C. to 100° C. and a pressure of less than or equal to 101 kPa for a minimum of 2 hours, and heating the resulting impregnated support in an oxidizing atmosphere at a temperature from 450° C. to 850° C. for a time not less than 2 hours.

2. The process according to claim 1, wherein the medium is selected from the group consisting of benzene, toluene, methanol, ethanol, propanol, butanol, water and mixtures thereof.

3. The process according to claim 2, wherein the catalyst is dried at a pressure of less than 50 kPa.

4. The process according to claim 3, wherein the support has an average particle size from 5 to 25 mesh or spheres between 2 to 10 mm diameter, or extrudates 1/16" to 1/4", a surface area greater than 100 m²/g, and a pore volume from about 0.1 to 1.3 ml/g.

5. The process according to claim 4, wherein the support is alumina or titania.

6. The process according to claim 5, wherein the loading of metal on the catalyst is from 0.1 to 1.5 weight % based on the weight of the support.

7. The process according to claim 6, wherein the ionic complex is palladium acetate.

* * * * *